(12) United States Patent
Wei

(10) Patent No.: US 8,287,501 B2
(45) Date of Patent: Oct. 16, 2012

(54) PEN NEEDLE ASSEMBLY

(75) Inventor: Min Wei, Morris Plains, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 12/863,097

(22) PCT Filed: Jan. 13, 2009

(86) PCT No.: PCT/US2009/030800
§ 371 (c)(1),
(2), (4) Date: Sep. 28, 2010

(87) PCT Pub. No.: WO2009/091709
PCT Pub. Date: Jul. 23, 2009

(65) Prior Publication Data
US 2011/0022001 A1    Jan. 27, 2011

Related U.S. Application Data

(60) Provisional application No. 61/011,171, filed on Jan. 15, 2008.

(51) Int. Cl.
*A61M 5/32* (2006.01)
(52) U.S. Cl. ......... 604/198; 604/192; 604/195; 604/197
(58) Field of Classification Search .................. 604/192, 604/195, 197, 198, 181, 187, 196, 263
See application file for complete search history.

(56) References Cited

U.S. PATENT DOCUMENTS 6,482,176 B1 * 11/2002 Wich .............................. 604/117
6,605,067 B1 *  8/2003 Larsen .......................... 604/192
2003/0050602 A1 *  3/2003 Pettis et al. ................... 604/117
2005/0038392 A1 *  2/2005 DeSalvo ....................... 604/198
2005/0277895 A1 * 12/2005 Giambattista et al. ........ 604/198

FOREIGN PATENT DOCUMENTS

| EP | 0 494 057 A1 | 7/1992 |
| WO | 99/27986 A1 | 6/1999 |
| WO | 00/30705 A1 | 6/2000 |
| WO | 2006/123251 A1 | 11/2006 |

* cited by examiner

*Primary Examiner* — Kevin C Sirmons
*Assistant Examiner* — Shefali Patel
(74) *Attorney, Agent, or Firm* — Hoffmann & Baron, LLP

(57) ABSTRACT

A pen needle assembly is provided herein having a hub with a distal end and a proximal end; a needle fixed to the hub and having a distal end, for insertion into a patient, and a proximal end; an inner shield disposed proximally of the hub; a spring disposed between the inner shield and the hub and configured to bias the hub distally; an outer shield with a distal end, a proximal end, and a tubular body at least partially encircling a portion of the needle with at least portions located radially outward further from the needle than the inner shield such that the outer shield at least partially encases the hub, the needle, the inner shield, and the spring; and a releasable retaining assembly configured to releasably retain the hub in a first locked state against the biasing of the spring. The distal end of the needle is covered by the outer shield with the hub being in the first locked state. Upon release of the releasable retaining assembly, the hub moves under force of the spring to an unlocked second state. In the unlocked second state, the distal end of the needle extends distally from the distal end of the outer shield. Advantageously, with the arrangement of the subject invention, an injection may be conducted properly by a person apprehensive of seeing a needle during a medical injection and may also help the person insert the needle at a proper angle.

8 Claims, 7 Drawing Sheets

PEN NEEDLE ASSEMBLY

This application is a National Stage Application under 35 U.S.C. §371 of PCT Application No. PCT/US2009/030800, filed Jan. 13, 2009, which claims priority to U.S. Provisional Patent Application No. 61/011,171, filed Jan. 15, 2008.

FIELD OF THE INVENTION

This invention relates to pen needle assemblies, more particularly, to pen needle assemblies for automatic injections.

BACKGROUND OF THE INVENTION

Pen injectors are known in the prior art and typically include a dose-adjustment mechanism for setting a dose of a drug, for example insulin, and a pen needle for insertion into a patient to allow proper drug administration. Such pens may be disposable, containing a single dose of a drug, or reusable, containing a single dose or more of a drug. The pen needle should be single-use and replaced with each administered dose. The pen needle includes a distal end formed for insertion into a patient and a proximal end for insertion into a drug vial or cartridge located inside the pen injector body.

Many people have "needle phobia" and are apprehensive of seeing a needle during a medical injection. As a result, people with "needle phobia" may not regularly administer drugs as prescribed or may improperly conduct an injection due to their apprehension. In addition, current pen needles may require a patient to insert a needle into their skin with a needle exposed. Current pen needle assemblies may be prone to improper insertion, e.g., insufficient insertion, into a person's skin because the needle may be inserted at an improper angle.

SUMMARY OF THE INVENTION

A pen needle assembly is provided herein having a hub with a distal end and a proximal end; a needle fixed to the hub and having a distal end, for insertion into a patient, and a proximal end; an inner shield disposed proximally of the hub; a spring disposed between the inner shield and the hub and configured to bias the hub distally; an outer shield with a distal end, a proximal end, and a tubular body at least partially encircling a portion of the needle with at least portions located radially outward further from the needle than the inner shield such that the outer shield at least partially encases the hub, the needle, the inner shield, and the spring; and a releasable retaining assembly configured to releasably retain the hub in a first locked state against the biasing of the spring. The distal end of the needle is covered by the outer shield with the hub being in a first locked state. Upon release of the releasable retaining assembly, the hub moves under force of the spring to an unlocked second state. In the unlocked second state, the distal end of the needle extends distally from the distal end of the outer shield. Advantageously, with the arrangement of the subject invention, an injection may be conducted properly by a person apprehensive of seeing a needle during a medical injection and may also help a person insert the needle at the proper angle.

These and other features of the invention will be better understood through a study of the following detailed description and accompanying drawings.

DETAILED DESCRIPTION OF THE DRAWINGS

Figure 1A:
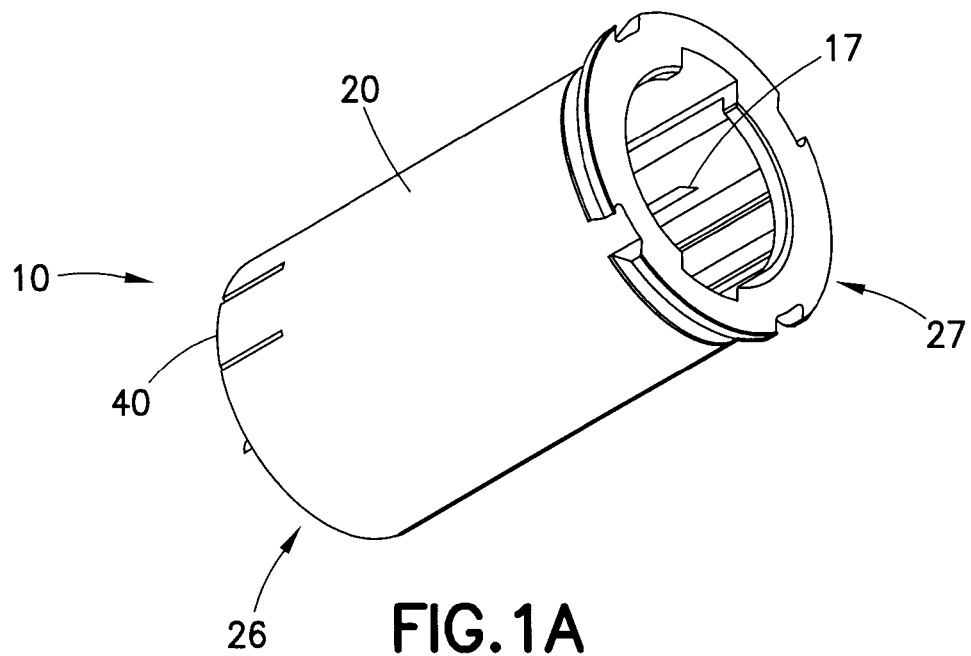
FIGS. 1A-1B depict the pen needle assembly of the present invention.
Figure 1B:
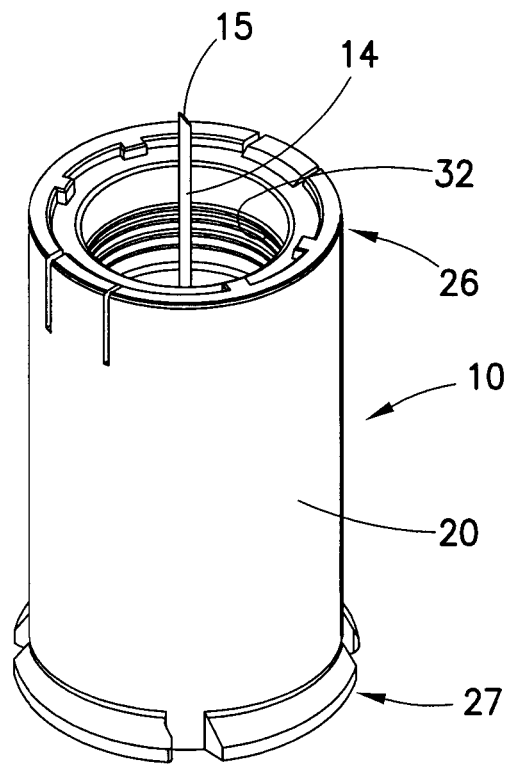
Figure 2:
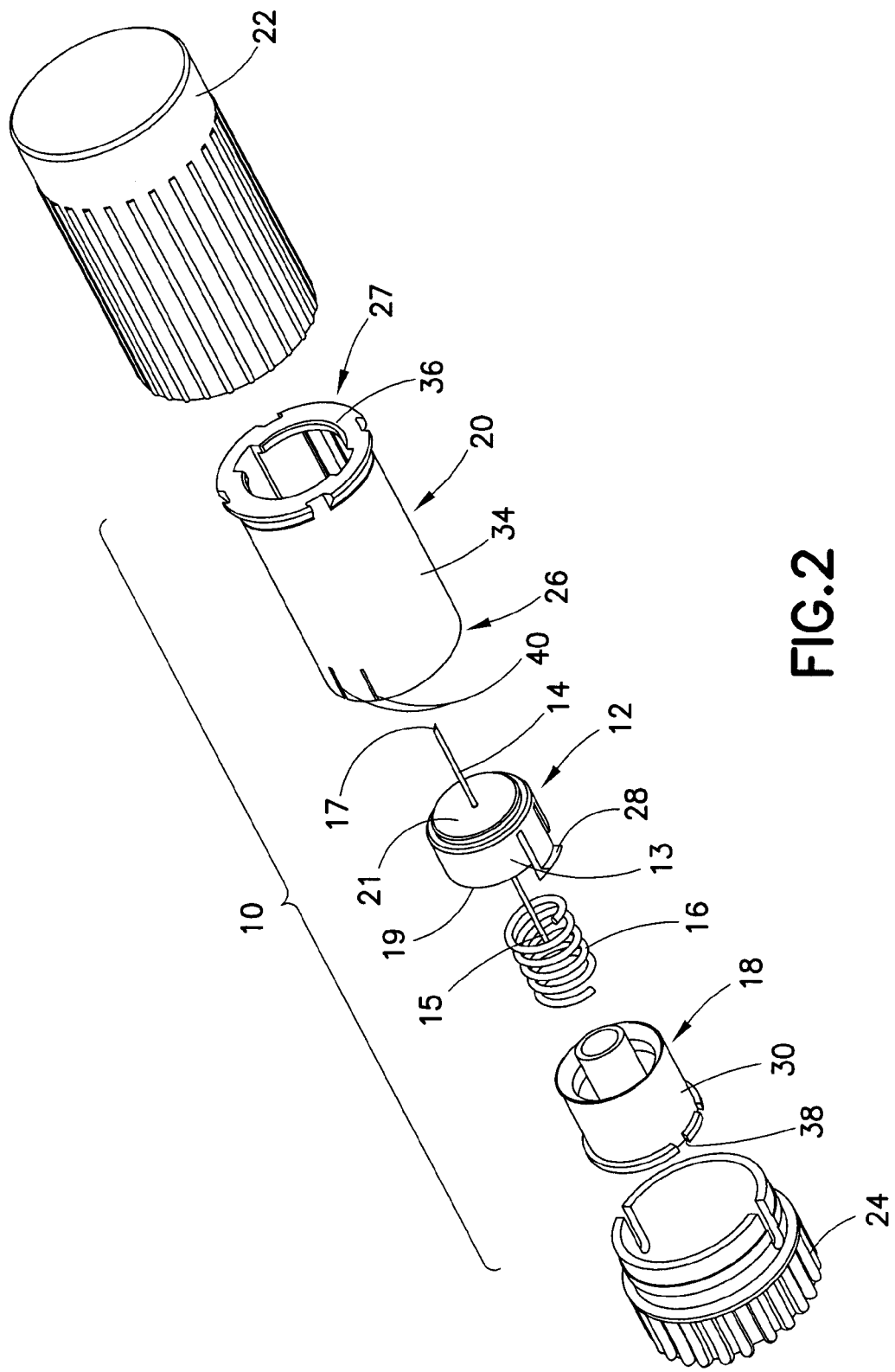
FIG. 2 depicts an exploded view of the pen needle assembly of the subject invention.

With reference to the Figures, a pen needle assembly 10 is provided herein. The assembly 10 generally includes a hub 12, a needle 14, a spring 16, an inner shield 18, and an outer shield 20, as shown in FIGS. 1A, 1B and 2. FIG. 2 also shows an outer cap 22 and an end cap 24 that may be used to store the pen needle assembly 10 prior to and after use. As described below, the assembly 10 is configured to shield the needle 14, allowing the injection to occur without the user viewing the needle 14 before use or inserting the needle 14 at an improper angle.

The needle 14 may be of any known type. Preferably, the needle 14 may have a length of less than 8 mm. The needle 14 includes a proximal end 15 and a distal end 17, formed for insertion into a patient. A lumen is defined between the proximal and distal ends 15, 17 for conveying medicament through the needle 14. The needle 14 is mounted to the hub 12 using any known technique.

The hub 12 includes a tubular body 13, which extends between a proximal end 19 and a distal end 21, and a releasable retaining assembly 28 for cooperative engagement with the inner shield 18 and the outer shield 20, such that a predetermined extent of proximal movement of the outer shield 20 relative to the inner shield 18, releases the hub 12 and the spring 16. The spring 16 may be located between the proximal end 19 of the hub 12 and the inner shield 18.

The inner shield 18 includes a tubular body 30 that at least partially encircles the needle 14 and fits inside the outer shield 20. The inner shield 18 may include a mounting assembly 32, such as threads, configured to cooperatively engage an associated pen injector body 42, such as described below.

The outer shield 20 includes a tubular body 34, which extends between a proximal end 26 and a distal end 27, and a rib 36 on the distal end 27 of the outer shield 20. The rib 36 provides a stable surface for contact with a person's skin at the time of injection and assists in providing proper insertion of the needle 14.

The inner shield 18 and the outer shield 20 may be provided with a cooperating shoulder 38 and tab 40 for limiting separation of the inner shield 18 from the outer shield 20. The tab 40 is formed to interferingly engage against the shoulder 38 such that relative movement between the inner shield 18 and the outer shield 20 is limited. In particular, this arrangement provides resistance against excessive proximal movement of the inner shield 18 under force of the spring 16. The shoulder 38 may be located on the inner shield 18 and the tab 40 may be located on the outer shield 20. Alternatively, the shoulder 38 may be located on the outer shield 20 and the tab 40 may be located on the inner shield 18.

Figure 3:
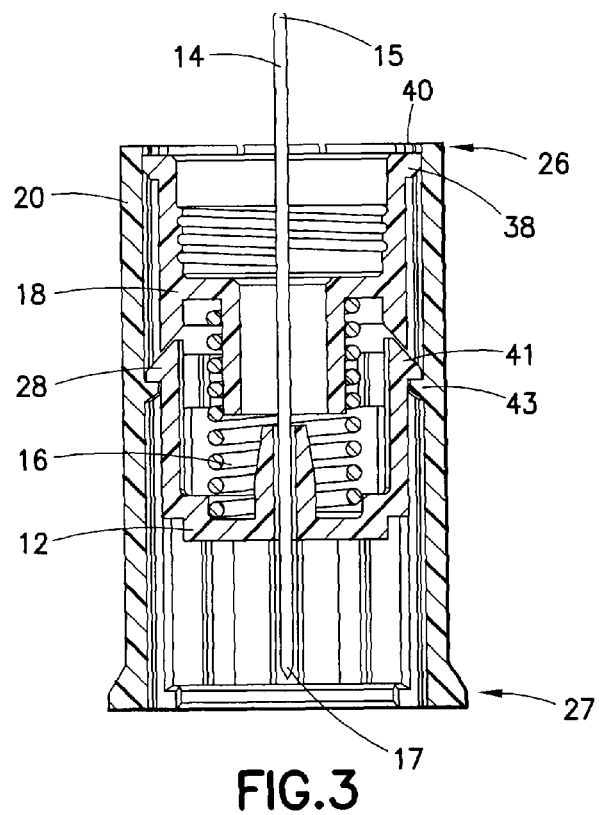
FIGS. 3-4 depict the pen needle assembly in a first locked state with the hub locked to the outer shield.
Figure 4:
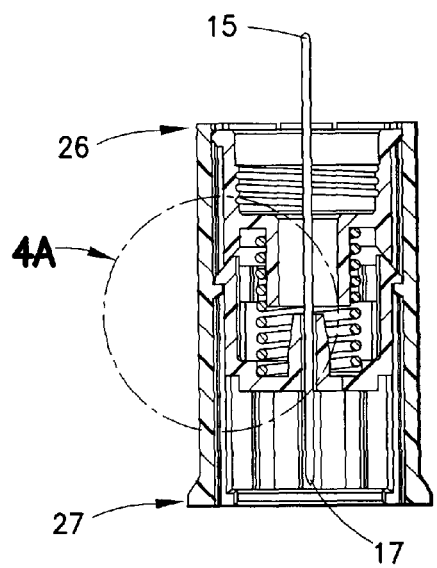
Figure 4A:
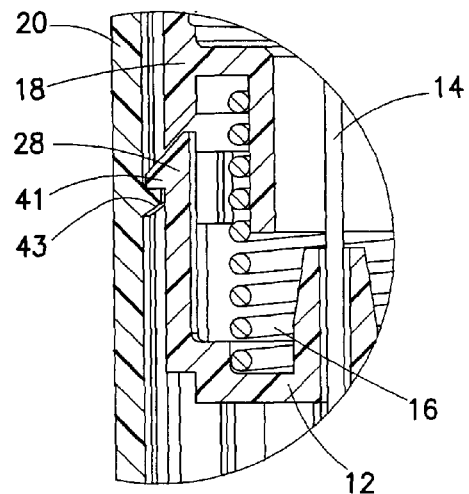
FIG. 4A is an enlarged view of section 4A of FIG. 4.

With reference to FIGS. 3, 4 and 4A, the pen needle assembly 10 is shown with the hub 12 in a first locked state. In the first locked state, the distal end 17 of the needle 14 is covered by the outer shield 20. The hub 12 is retained in the first locked state 12, against biasing force of the spring 16, by the releasable retaining assembly 28. In particular, the releasable retaining assembly 28 includes deflectable latches 41 formed on the hub 12 which are formed to engage a shoulder 43 formed on the outer shield 20. The interengagement of the latches 41 and the shoulder 43 restricts distal movement of the hub 12 under force of the spring 16.

Figure 5:
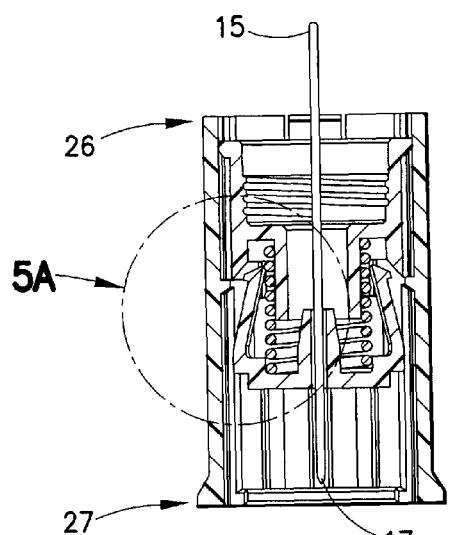
FIG. 5 depicts the pen needle assembly with the hub releasing from a first locked state.
Figure 5A:
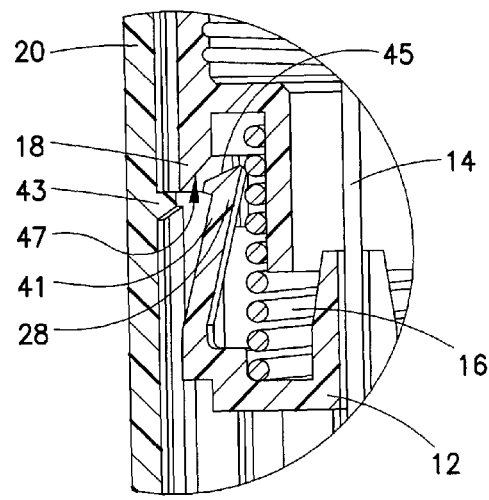
FIG. 5A is an enlarged view of section 5A of FIG. 5.
Figure 6:
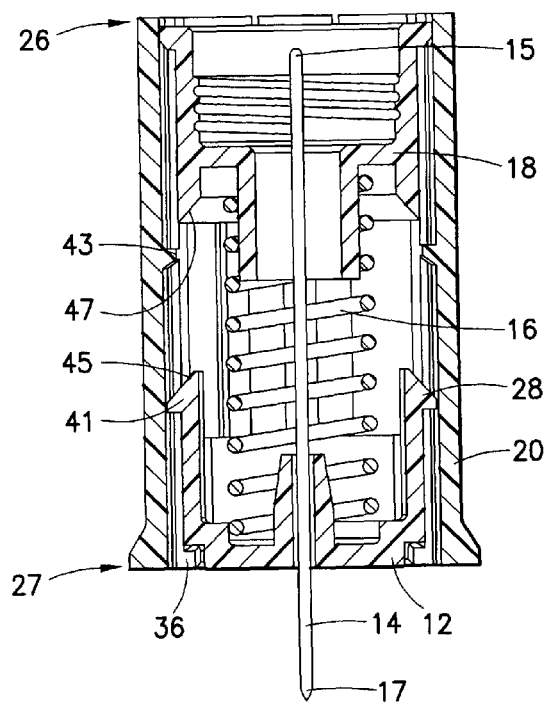
FIG. 6 depicts the pen needle assembly with the hub in a second unlocked state.

FIGS. 5 and 6 show the pen needle assembly 10 during an injection. In FIG. 5, the releasable retaining assembly 28 is shown released. Various configurations can be provided to release the releasable retaining assembly 28. By way of non-limiting example, and in a preferred arrangement, the latches 41 are provided with outwardly tapered engagement surfaces 45. Correspondingly, the inner shield 18 is provided with distally-directed tapered actuation surfaces 47. The actuation surfaces 47 are aligned to axially register with the engagement surfaces 45. It is preferred that the engagement surfaces 45 and the actuation surfaces 47 have opposing orientations, such that, as shown in the FIGS. 4A and 5A, a predetermined extent of relative movement between the two elements (particularly, movement of the engagement surfaces 45 and the actuation surfaces 47 towards each other) results in inward displacement of the latches 41. Relative movement between the hub 12 and the inner shield 18 may be caused when the outer shield 20 is pressed against a patient's skin during an injection. With the outer shield 20 being held against a patient's skin, pressure applied to the hub 12 (from the user via the injector) causes downward displacement of the inner shield 18. With the hub 12 being restricted from distal movement, as described above, the inner shield 18 moves relative to the hub 12 and causes the engagement surfaces 45 and the actuation surfaces 47 to come into contact. With the opposing tapered configurations of the engagement surfaces 45 and the actuation surfaces 47, further displacement of the inner shield 18 causes the latches 41 to inwardly displace (as shown in FIG. 5A). With the latches 41 inwardly displaced, the hub 12 moves distally under force of the spring 16 to the state shown in FIG. 6.

With reference to FIG. 6, the pen needle assembly 10 is shown in the second unlocked state, with the hub 12 at the distal end 27 of the outer shield 20 and the distal end 17 of the needle 14 extended beyond the distal end 27 of the outer shield 20 for injection. Distal movement of the hub 12 may be restricted by a patient's skin and/or by interengagement between the hub 12 and the rib 36 projecting around the distal end 27 of the outer shield 20.

Figure 7:
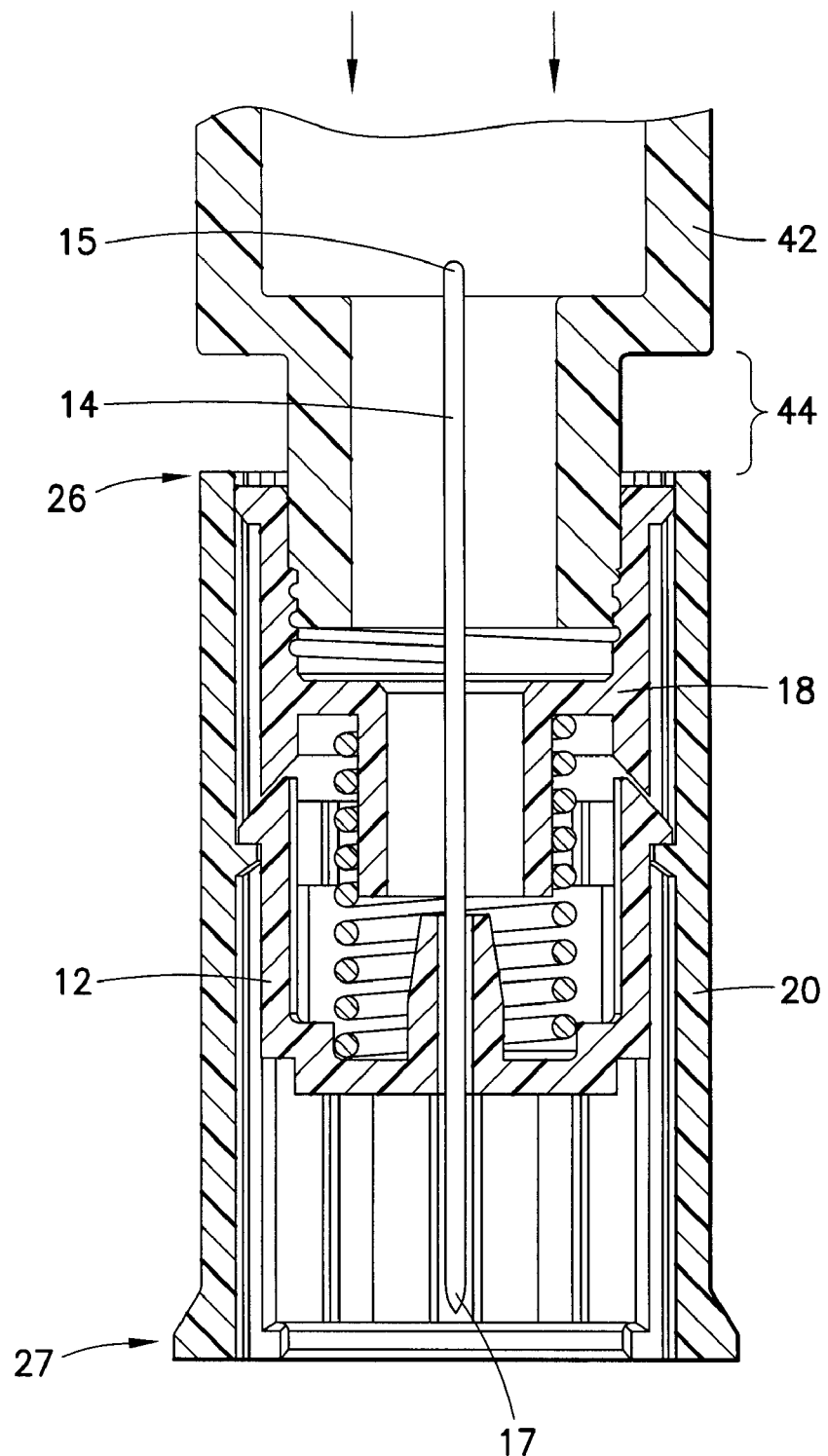
FIG. 7 depicts the pen needle assembly attached to an injector body.

With reference to FIG. 7, the pen needle assembly 10 is shown attached to the pen injector body 42. The pen needle assembly 10 may be attached to the injector body 42 such that a gap 44 is defined between the outer shield 20 and a portion of the injector body 42. The gap 44 may remain until the needle 14 releases. During use, the gap 44 may decrease as pressure is applied to the injector and the inner shield 18 is displaced distally as described above during an injection. The gap 44 may be configured such that the gap 44 is eliminated with the hub 12 being released (i.e., the gap 44 is eliminated with the needle 14 being inserted into the patient). The gap 44, or lack thereof, may provide an indication of the status of an injection.

After use, the pen needle assembly 10 remains in the state shown in FIG. 6. The pen needle assembly 10 may be removed from the injector body 42 for disposal or may be disposed of with the injector body 42. The pen needle assembly 10 may be removed by unthreading or by providing any other release action that the release mechanism 32 may require.

Figure 8A:
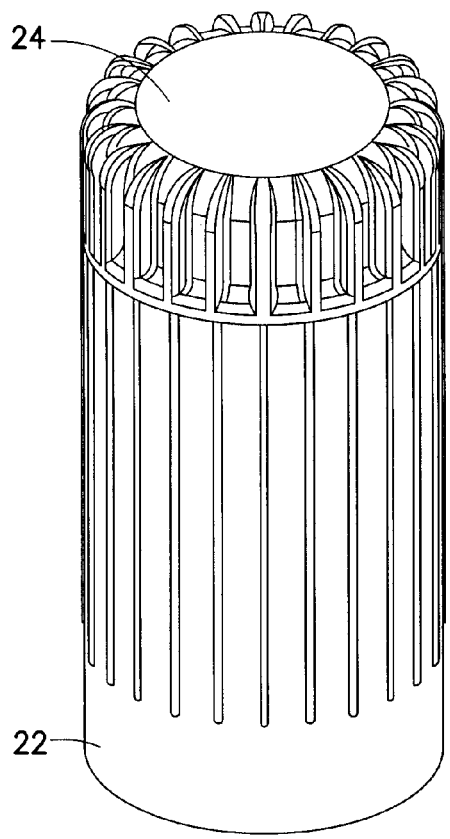
FIGS. 8A-8B depicts a cap for the pen needle assembly of the present invention.
Figure 8B:
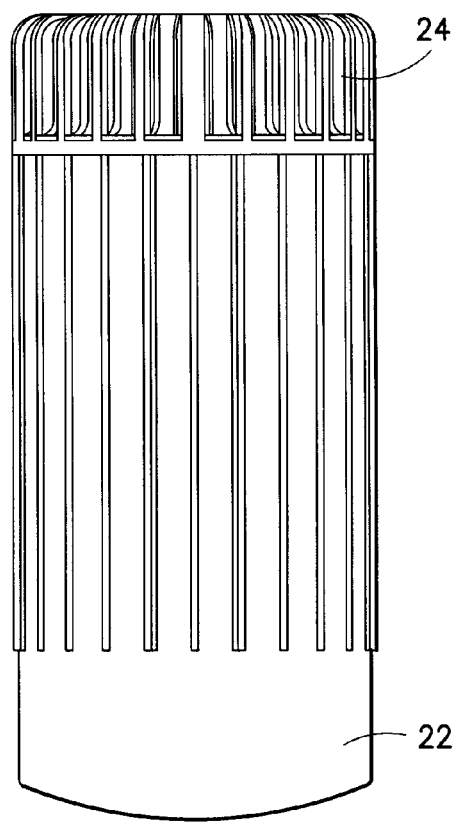
Figure 9:
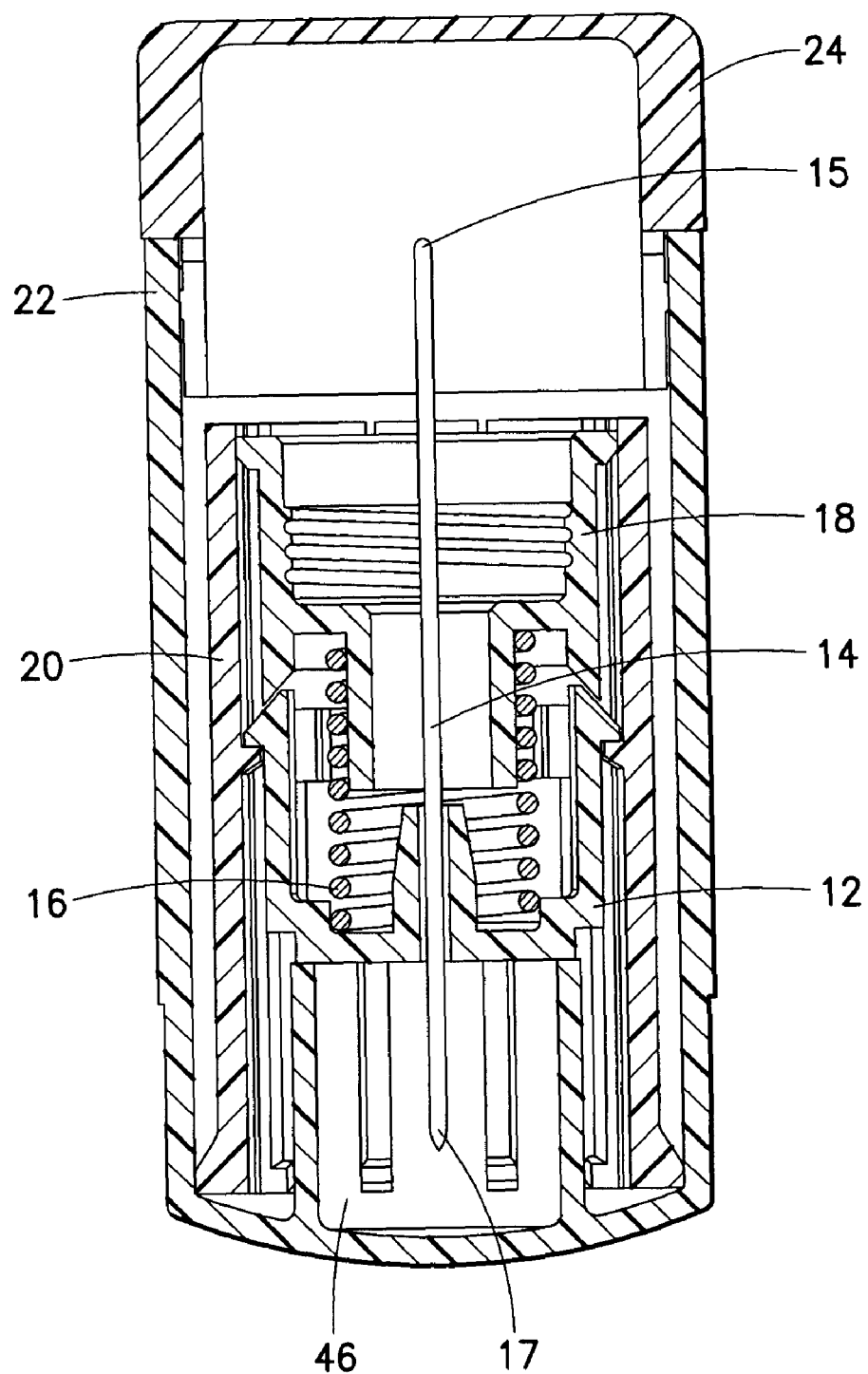
FIG. 9 depicts a cross-section of the pen needle assembly of the present invention with the cap encasing the pen needle assembly.

FIGS. 8A and 8B show the outer cap 22 and the end cap 24 for encasing the pen needle assembly 10 before and/or after use. With reference to FIG. 9, the outer cap 22 and the end cap 24 is shown fully encasing the pen needle assembly 10 along with the needle 14. Before use, the assembly of FIG. 9 may be provided in a sterile state. After use, the outer cap 22 may be inserted onto the pen needle assembly 10 to cover the needle 14 which is in a used state. A protruding reset element 46 may be provided in the outer cap 22 configured to push against the hub 12 and the spring 16 proximally as the pen needle assembly 10 is inserted into the outer cap 22. Under this action, the reset element 46 may cause the releasable retaining assembly 28 to re-engage with the pen needle assembly 10 returning to the first locked state, as shown in FIGS. 3 and 4.

What is claimed is:

1. A pen needle assembly comprising:
a hub having a distal end and a proximal end;
a needle fixed to said hub, said needle having a distal end, formed for insertion into a patient, and a proximal end;
an inner shield disposed proximally of said hub;
a spring disposed between said inner shield and said hub configured to bias said hub distally;
an outer shield having a distal end and a proximal end and a tubular body at least partially encircling a portion of said needle; said outer shield having at least portions located radially outward further from said needle than said inner shield such that said outer shield at least partially encases said hub, said needle, said inner shield, and said spring; and
a releasable retaining means configured to releasably retain said hub in a first locked state against said biasing of said spring,
wherein, said distal end of said needle is covered by said outer shield with said hub being in the first locked state, wherein, upon release of said releasable retaining means, said hub moves under force of said spring to a second unlocked state, and, wherein, in said second unlocked state, said distal end of said needle extends distally from said distal end of said outer shield, and
wherein a predetermined extent of proximal movement of said outer shield, relative to said inner shield, causes said releasable retaining means to release said hub.

2. A pen needle assembly as in claim 1, wherein said inner shield has a tubular body at least partially encircling a portion of said needle.

3. A pen needle assembly as in claim 1, further comprising a mounting means for mounting said pen needle assembly onto an injector body.

4. A pen needle assembly as in claim 3, wherein said mounting means includes threads formed on said inner shield.

5. A pen needle assembly as in claim 1, further comprising at least one rib on said outer shield, wherein said at least one rib prevents said hub from detaching from said outer shield.

6. A pen needle assembly as in claim 1, wherein a needle length between the distal end of said outer shield and the distal end of said needle is less than 8 mm.

7. A pen needle assembly of claim 1, further comprising:
an outer cap, tubular in shape; and
an end cap, tubular in shape;

wherein, said end cap is attachable to said outer cap such that said outer cap and said end cap surround said pen needle assembly and cover the proximal and distal ends of said needle.

8. An automatic injector comprising:
said pen needle assembly as in claim 1; and
an injector body;
wherein a gap exists between said pen needle assembly and said injector body when said pen needle assembly is in said first locked state, said gap being eliminated with said hub moving to said second unlocked state.

\* \* \* \* \*